US012023478B2

(12) United States Patent
Khalpey et al.

(10) Patent No.: US 12,023,478 B2
(45) Date of Patent: Jul. 2, 2024

(54) DUAL LUMEN CANNULA SYSTEM

(71) Applicants: ARIZONA BOARD OF REGENTS ON BEHALF OF THE UNIVERSITY OF ARIZONA, Tucson, AZ (US); Banner University Medical Group, Phoenix, AZ (US)

(72) Inventors: Zain I. Khalpey, Tucson, AZ (US); Zachary David Frankman, Tucson, AZ (US); David A. Bull, Tucson, AZ (US); Marvin J. Slepian, Tucson, AZ (US); Richard G. Smith, Tucson, AZ (US)

(73) Assignees: ARIZONA BOARD OF REGENTS ON BEHALF OF THE UNIVERSITY OF ARIZONA, Tucson, AZ (US); BANNER UNIVERSITY MEDICAL GROUP, Phoenix, AZ (US)

( * ) Notice: Subject to any disclaimer, the term of this patent is extended or adjusted under 35 U.S.C. 154(b) by 910 days.

(21) Appl. No.: 17/047,955

(22) PCT Filed: Apr. 25, 2019

(86) PCT No.: PCT/US2019/029083
§ 371 (c)(1),
(2) Date: Oct. 15, 2020

(87) PCT Pub. No.: WO2019/210043
PCT Pub. Date: Oct. 31, 2019

(65) Prior Publication Data
US 2022/0257845 A1    Aug. 18, 2022

Related U.S. Application Data

(60) Provisional application No. 62/662,418, filed on Apr. 25, 2018.

(51) Int. Cl.
*A61M 1/36* (2006.01)
*A61M 1/16* (2006.01)
(Continued)

(52) U.S. Cl.
CPC ........ *A61M 60/268* (2021.01); *A61M 1/1698* (2013.01); *A61M 1/3659* (2014.02);
(Continued)

(58) Field of Classification Search
CPC ............ A61M 25/0026; A61M 25/007; A61M 25/0071; A61M 2025/0004;
(Continued)

(56) References Cited

U.S. PATENT DOCUMENTS 4,129,129 A * 12/1978 Amrine ............... A61M 1/3659
600/16
4,552,552 A    11/1985 Polaschegg et al.
(Continued)

FOREIGN PATENT DOCUMENTS

CA    2349627 A1    5/2000

OTHER PUBLICATIONS

Chimot et al. "Avalon Bicaval Dual-Lumen Cannula for Venovenous Extracorporeal Membrane Oxygenation: Survey of Cannula Use in France," Respiratory Support, ASAIO Journal 2013, pp. 157-161.

*Primary Examiner* — Robert J Utama
*Assistant Examiner* — Justin L Zamory
(74) *Attorney, Agent, or Firm* — NGUYEN TARBET LLC

(57) ABSTRACT

Systems and methods for providing oxygenated blood to a patient, e.g., in a patient with inadequate or failing circulation, including a dual lumen cannula system for drawing blood from the heart and returning oxygenated blood therein. Methods may feature inserting the dual lumen cannula system through the left ventricle such that intake
(Continued)

aperture are positioned entirely within the left ventricle and the tip of the cannula is positioned in the aorta of the patients heart. By fluidly connecting the cannula to a cardiac assistance device, deoxygenated blood may be drained from the left ventricle through the intake apertures and oxygenated blood may be pumped into the aorta thorough the tip.

6 Claims, 6 Drawing Sheets

(51) Int. Cl.
    *A61M 60/113*     (2021.01)
    *A61M 60/268*     (2021.01)
    *A61M 60/38*     (2021.01)
    *A61M 60/857*     (2021.01)

(52) U.S. Cl.
    CPC .......... *A61M 60/113* (2021.01); *A61M 60/38* (2021.01); *A61M 60/857* (2021.01)

(58) Field of Classification Search
    CPC .. A61M 60/268; A61M 60/38; A61M 60/113; A61M 60/857; A61M 1/3659; A61M 1/1698
    See application file for complete search history.

(56) References Cited

U.S. PATENT DOCUMENTS

| | | | | |
|---|---|---|---|---|
| 5,147,388 | A * | 9/1992 | Yamazaki | A61M 60/237 623/3.13 |
| 5,222,980 | A | 6/1993 | Gealow | |
| 5,814,102 | A | 9/1998 | Guldner et al. | |
| 6,709,418 | B1 | 3/2004 | Aboul-Hosn et al. | |
| 7,524,277 | B1 | 4/2009 | Wang et al. | |
| 9,717,830 | B2 | 8/2017 | Farnan | |
| 9,782,534 | B2 | 10/2017 | Kelly et al. | |
| 2006/0155158 | A1* | 7/2006 | Aboul-Hosn | A61M 60/178 600/16 |
| 2010/0152707 | A1* | 6/2010 | Morris | A61M 1/84 604/523 |
| 2011/0245916 | A1 | 10/2011 | Min et al. | |
| 2011/0319816 | A1 | 12/2011 | von Segesser | |
| 2013/0158338 | A1* | 6/2013 | Kelly | A61M 25/007 600/16 |
| 2013/0218077 | A1 | 8/2013 | Cox | |
| 2014/0163664 | A1 | 6/2014 | Goldsmith | |
| 2014/0275724 | A1 | 9/2014 | Wang et al. | |
| 2015/0223923 | A1 | 8/2015 | Forsell | |
| 2016/0082176 | A1 | 3/2016 | Kelly et al. | |
| 2016/0095972 | A1 | 4/2016 | Shorey | |

\* cited by examiner

PRIOR ART

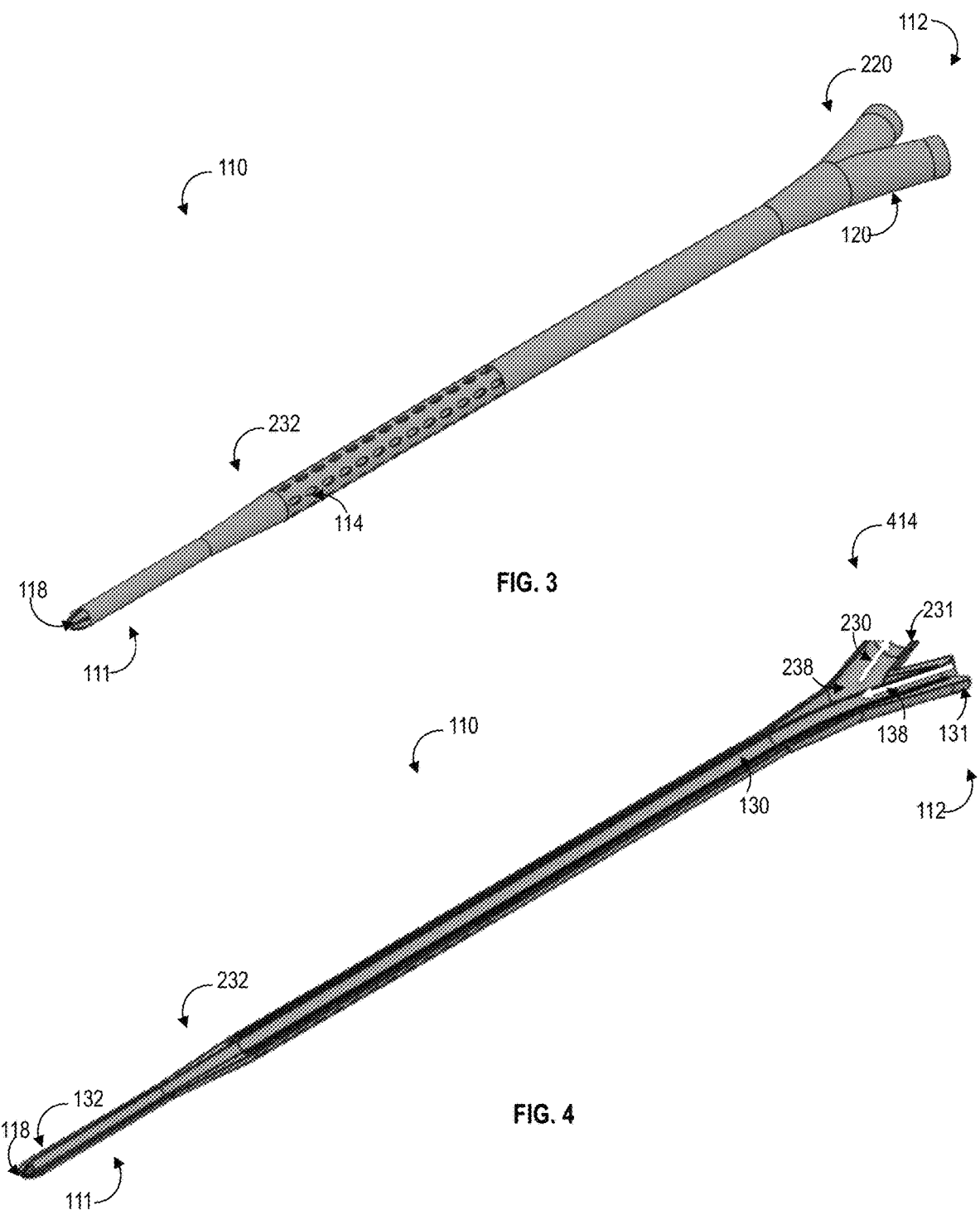

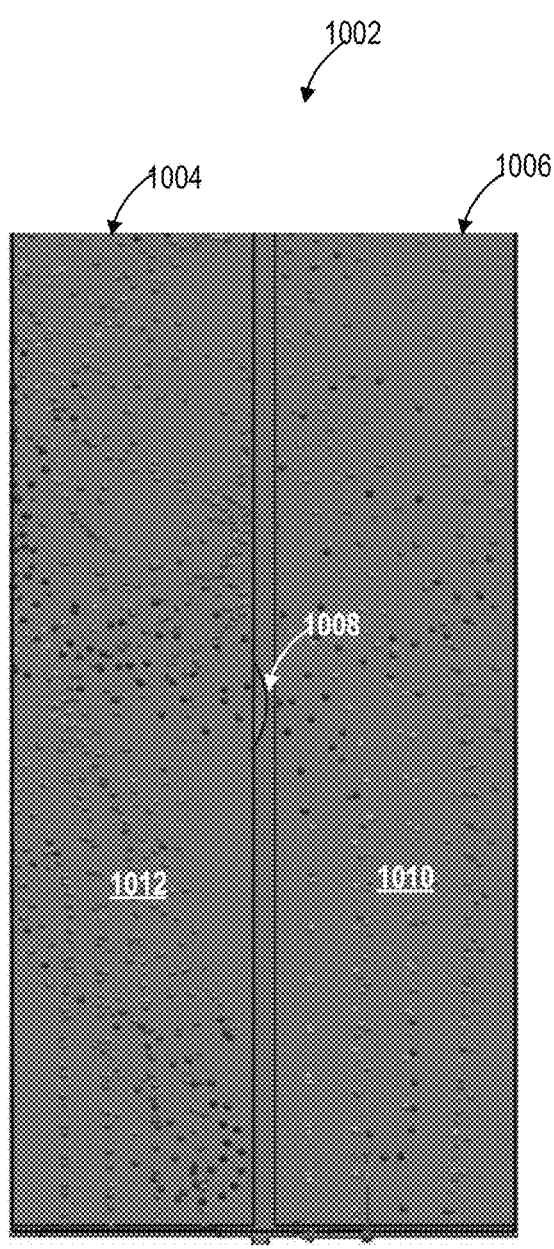
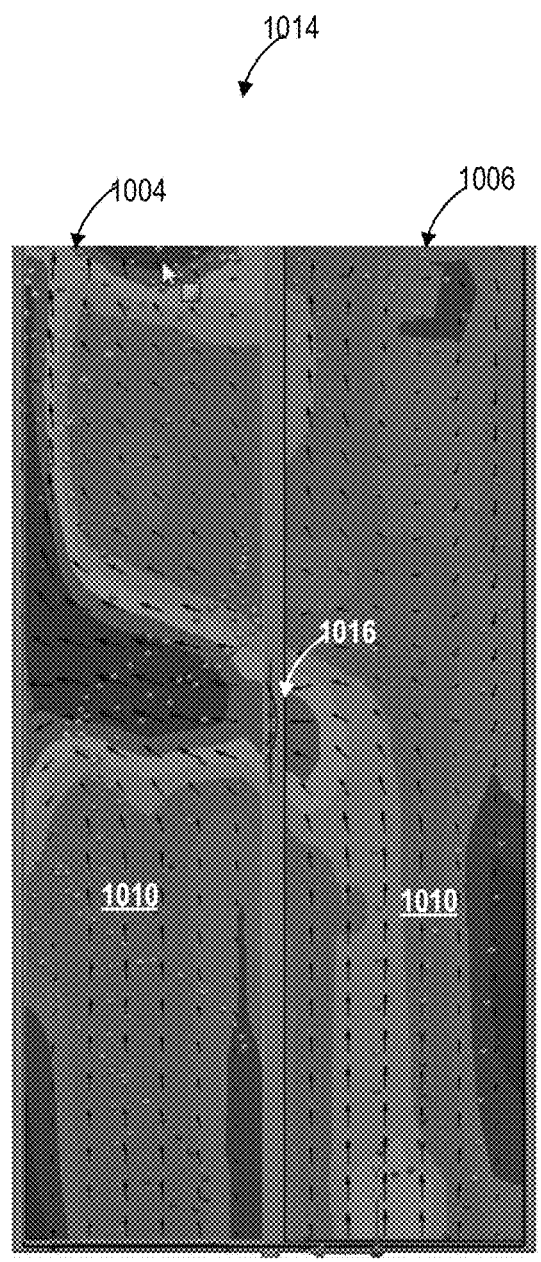
FIG. 8A
FIG. 8B

DUAL LUMEN CANNULA SYSTEM

CROSS-REFERENCES TO RELATED APPLICATIONS

This application claims benefit of U.S. Patent Application No. 62/662,418, filed Apr. 25, 2018, the specification of which is incorporated herein in its entirety by reference.

BACKGROUND OF THE INVENTION

Field of the Invention

The present invention relates to systems and methods for providing oxygenated blood to a patient, e.g., in a patient with inadequate or failing circulation. More particularly, the present invention relates to cannulas for drawing blood from the heart and returning oxygenated blood therein.

Background Art

Biventricular assist device insertion is a feasible surgical treatment option for refractory cardiogenic shock. Cardiopulmonary bypass through a median sternotomy in a patient with failing circulation can induce profound coagulopathy and systemic inflammation, necessitating multiple blood transfusions and leading to various pathologies later. Minimizing surgical trauma and allowing early postoperative ambulation may optimize outcomes in these patients.

Traditional venoarterial extracorporeal membrane oxygenation (VA ECMO) is the current standard of care used to treat right ventricular failure and respiratory failure percutaneously. In a typical VA ECMO procedure, e.g., as shown in FIG. 1, a prior art cannula (40) is inserted through the neck vain into the superior vena cava and the right atrium (80), and through the tricuspid valve, into the right ventricle and then into the pulmonary artery (90). The prior art cannula (40) is then connected to the extracorporeal membrane oxygenation (ECMO) device that removes blood from the right atrium and oxygenates the blood, and returns the oxygenated blood to the pulmonary artery.

One of the most important issues occurring with VA ECMO is retrograde aortic flow, which causes an increase in the left ventricular (LV) afterload leading to left ventricular (LV) distension. As such, LV distention can lead to severe pulmonary edema, increased wall stress, cause stagnation of blood and formation of clots in the heart chambers, and delay ventricular recovery. In view of these issues, there is a need for a cardiac procedure to reduce LV distention.

BRIEF SUMMARY OF THE INVENTION

The present invention discloses a dual lumen cannula system and methods of use, wherein the cannula system can be used to provide oxygenated blood to a patient. The system can reduce left ventricular distention and function as a bridge to a decision, an explant or an implantable device.

For example, the present invention provides a dual lumen cannula system for insertion into a patient's heart. In certain embodiments, the system, e.g., the cannula, comprises a first tube and a second tube formed from bifurcation of a proximal end of the cannula; a tip disposed at a distal end of the cannula, the tip comprises at least one slot; and intake apertures disposed in a side wall of the cannula a distance from the tip, wherein the intake apertures are oval in shape. The cannula further comprises a first lumen extending through the first tube and the cannula, wherein the first lumen has a first end for fluidly connecting to a cardiac assistance device and a second end fluidly connected to the at least one slot in the tip of the cannula. Blood can pass from the first lumen to outside the cannula via the at least one slot in the tip. The cannula further comprises a second lumen extending through the second tube and at least a portion of the cannula, wherein the second lumen has a first end for fluidly connecting to a cardiac assistance device and a second end fluidly connected to the intake apertures in the side wall of the cannula. Blood can pass from outside the cannula to the second lumen via the intake apertures. The first lumen is sealed from the second lumen.

In some embodiments, an inner wall of the second tube defines the first end of the second lumen. In some embodiments, an inner wall of the cannula and an outer wall of the first lumen define the second lumen.

In some embodiments, the tip of the cannula comprises a center slot. In some embodiments, the at least one slot comprises a plurality of slots that radially extend from the center slot in the tip of the cannula. In some embodiments, the center slot is for allowing passage of a guidewire. In some embodiments, the tip of the cannula can be positioned in an aorta without puncturing the aorta. In some embodiments, the tip comprises a plurality of tapering radial slits.

In some embodiments, the intake apertures extend for a threshold distance in the side wall of the cannula, wherein the threshold distance positions the intake apertures entirely within a left ventricle of the heart of the patient when the cannula is inserted through a left ventricle, an aortic valve, and a left atrium. In some embodiments, the intake apertures are configured to reduce a shear force applied to blood that flows in a left ventricle through the intake apertures.

In some embodiments, the system further comprises a cardiac assistance device (e.g., an extracorporeal pump) fluidly connected to the first end of the first lumen and to the first end of the second lumen. The cardiac assistance device may feature a pump and an oxygenator. The cardiac assistance device intakes deoxygenated blood from the second lumen, oxygenates said deoxygenated blood to form oxygenated blood, and pumps said oxygenated blood through the first lumen and out of the cannula via the tip.

The present invention also features a method of oxygenating blood of a patient. In certain embodiments, the method comprises using a dual lumen cannula system according to the present invention and a cardiac assistance device. The first end of the first lumen is fluidly connected to an outlet port of the cardiac assistance device and the first end of the second lumen is fluidly connected to an intake port of the cardiac assistance device.

The method may comprise, for example, inserting the tip of the cannula through a left ventricle, an aortic valve, and further through a left atrium of a heart of the patient such that the tip of the cannula is positioned in an aorta without puncturing the aorta. The intake apertures are positioned within the left ventricle. The method may further comprise circulating blood through the cannula and the cardiac assistance device, wherein deoxygenated blood from the left ventricle flows through the intake apertures and into the second lumen, the cardiac assistance device intakes the deoxygenated blood from the second lumen and oxygenates said deoxygenated blood to form oxygenated blood, and pumps said oxygenated blood through the first lumen. Oxygenated blood from the first lumen exits the cannula to the aorta via the tip, thereby providing oxygenated blood to the patient.

In some embodiments, the method reduces left ventricular distention in the patient. In some embodiments, the method reduces shearing of the blood. In some embodiments, the method reduces platelet activation.

In some embodiments, an inner wall of the second tube defines the first end of the second lumen. In some embodiments, an inner wall of the cannula and an outer wall of the first lumen define the second lumen.

In some embodiments, the tip of the cannula comprises a center slot. In some embodiments, the at least one slot comprises a plurality of slots that radially extend from a center slot in the tip of the cannula. In some embodiments, the center slot is for allowing passage of a guidewire. In some embodiments, the slots have a tapered shape.

In some embodiments, the intake apertures are oriented in a radial repeating pattern of a set of linear oval holes, wherein the set of linear oval holes extends for a threshold distance in the side wall of the cannula and the threshold distance positions the intake apertures entirely within the left ventricle of the heart. In some embodiments, the intake apertures are positioned in the side wall of the cannula such that a major axis of each of the intake apertures is along a direction of a flow of blood flowing in the second lumen. In some embodiments, a ratio of a major axis and a minor axis of each intake aperture is a ratio from 2 to 2.5.

In some embodiments, the cardiac assistance device comprises electric pressure sensors to regulate intake of blood and output of blood.

The system and methods herein may be used for providing oxygenated blood to a patient, e.g., in a patient with inadequate or failing circulation. By fluidly connecting the cannula to a cardiac assistance device, deoxygenated blood may be drained from the left ventricle through the intake apertures and oxygenated blood may be pumped into the aorta thorough the tip.

One of the unique and inventive technical features of the present invention is the insertion of the cannula into the left ventricle to drain blood accumulated in the left ventricle through apertures positioned in the left ventricle, and to deliver oxygenated blood to the aorta through a tip of the cannula positioned in the aorta. Most surgeons would attempt to defibrillate or otherwise resuscitate a patient in cardiac arrest or would put the patient on ECMO by drawing and expelling blood using arteries and veins due to their ease of access. These are invasive and can produce inconsistent outcomes, and additionally, when the patient is placed on ECMO, the resistance to flow experienced by the arteries and veins is high; as a result, the heart's valves must be kept open by fluid pressure alone, which can be unreliable. By using a percutaneous or transapical cannula of the present invention, the valves of the heart may be physically kept open. This helps make the pumping of blood through the valves more reliable and results in directly pressurizing the aorta and maintaining blood flow through the patient's heart. In addition, by placing the cannula of the present invention in the left ventricle, blood accumulated in the left ventricle is drained consistently and reliably through the plurality of apertures, thereby reducing LV distention and producing consistent outcomes.

It was surprisingly discovered that a particular geometry and shape of the intake apertures and slots could reduce shear forces on the blood flowing through them. If exposed to high shear forces, platelets can be activated to begin the clotting cascade, which is an undesired effect. One of ordinary skill in the art would expect that an oval-shaped aperture would require higher pressure gradient to achieve a certain flow, and hence would result in greater shear forces. This led to some disbelief in the field that it would be possible to make the shape of the holes oval or oblong and still achieve reduced shear forces. Unexpectedly and surprisingly, simulations performed using oval-shaped holes of the cannula show that shear forces are in fact reduced. Without wishing to limit the present invention to any theory or mechanism, it is believed that the oval-shaped intake apertures and the tapered shape of the slots in the tip of the cannula result in reducing shearing forces experience by the blood entering and exiting the cannula, thereby providing a hemodynamic way to reduce LV distention. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 3 shows a perspective view of the cannula of the system of the present invention.

FIG. 4 shows a cross-sectional view of the cannula, showing a first lumen and a second lumen.

FIG. 8A shows a simulation view of blood flow through a circular intake aperture.

FIG. 8B shows a simulation view of blood flow through an oval-shaped intake aperture.

DETAILED DESCRIPTION OF THE INVENTION

Figure 1:
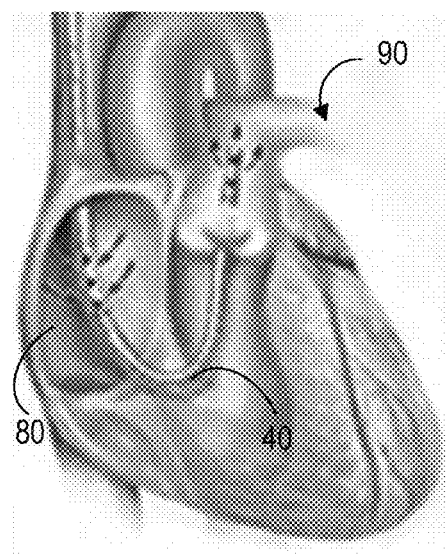
FIG. 1 shows a cannula of prior art inserted through a right side of the patient's heart.

Following is a list of elements corresponding to a particular element referred to herein:

40 prior art cannula
50 cardiac assistance device
60 left ventricle
70 aorta
80 right atrium
90 pulmonary artery
100 dual lumen cannula system
110 cannula 111 distal end of cannula
112 proximal end of cannula
114 intake apertures
118 tip of cannula
119a central hole
119b slots
119c outer edge of slot
120 first tube
130 first lumen
131 first end of first lumen
132 second end of first lumen
138 direction of blood flow in first lumen
220 second tube
230 second lumen
231 first end of second lumen
232 second end of second lumen
238 direction of blood flow in second lumen The present invention features systems and methods for providing oxygenated blood to a patient, e.g., in a patient with inadequate or failing circulation. For example, the system of the present invention is a dual lumen cannula system that can be used to draw blood from the heart and return oxygenated blood therein.

Figure 2:
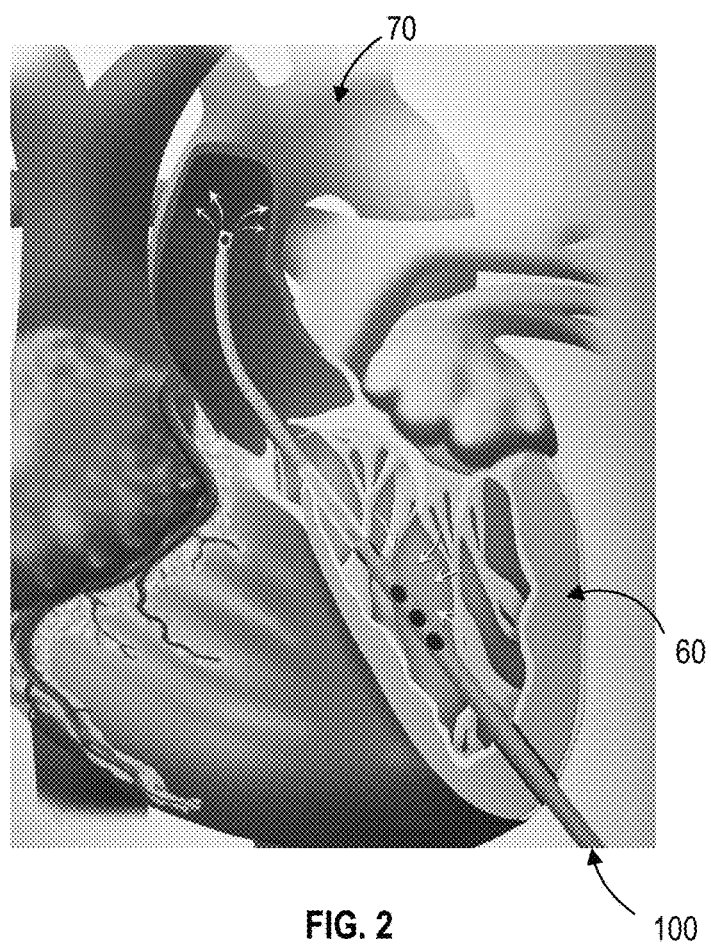
FIG. 2 shows a schematic view of the system of the present invention positioned inside the left side of a patient's heart.

Referring to FIG. 2, the dual lumen cannula system (100) of the present invention can be inserted into a left ventricle (e.g., into the left ventricle (60), through the aortic valve, and into the aorta (70)) of a patient's heart). The system (100) is fluidly coupled to a cardiac assistance device (50), which functions to oxygenate blood therein.

Referring to FIG. 3, FIG. 4, FIG. 5, and FIG. 6, the dual lumen cannula system (100) of the present invention comprises a cannula (110) having a distal end (111) and a proximal end (112), the distal end (111) being the end that is considered the tip or the end that is placed into the aorta. The proximal end (112) is bifurcated, forming a first tube (120) and a second tube (220).

The first tube (120) comprises a first channel (e.g., a first lumen (130)). The first lumen (130) may be defined by the tubular side wall of the first tube (110). In some embodiments, the first lumen (130) is formed by its own side wall (e.g., separate from the tubular side wall of the first tube (120). The first lumen (130) has a proximal end (131) that fluidly connects to the output of the cardiac assistance device (50). The first lumen (130) extends from its first end (131) through the cannula (110) and to a second end (132) at or near the distal end (111) (e.g., the tip (118)) of the cannula (110). Without wishing to limit the present invention to any theory or mechanism, the first end (131) of the first lumen (130) may be considered the input end and the second end (132) of the first lumen (130) may be considered the output end of the cannula (110) or system (100).

The tip (118) comprises at least one slot disposed therethrough. The slots may be arranged radially around a center of the tip (118), e.g., as shown in FIG. 3. The shape and arrangement of the slots is not limited to that of FIG. 3. Blood can be released from the first lumen (130) through the tip (118) of the cannula (110), e.g., after having passed through the cardiac assistance device (50).

The second tube (220) comprises a second channel (a second lumen (230)). The second lumen (230) may be defined by the tubular side wall of the second tube (220). In some embodiments, the second lumen (230) is formed by its own side wall (e.g., separate from the tubular side wall of the second tube (220). The second lumen (230) has a first end (231), which is fluidly connected to the input of the cardiac assistance device (50). The second lumen (230) extends from its first end (231) through at least a portion of the cannula (110) (alongside the first lumen (130)) to its second end (232). The second end (232) of the second lumen (230) is positioned a distance from the tip (118), e.g., as shown in FIG. 4. The second end (232) of the second lumen (230) fluidly connects to a plurality of intake apertures (114) disposed in at least a portion of the sidewall of the cannula (110). The intake apertures (114) may be slots, slits, round, oval-shaped, etc. The present invention is not limited to the configuration shown in FIG. 3 or FIG. 4. Blood can be taken in to the second lumen (230) via the intake apertures (114), e.g., to prepare for the cardiac assistance device (50).

Figure 5:
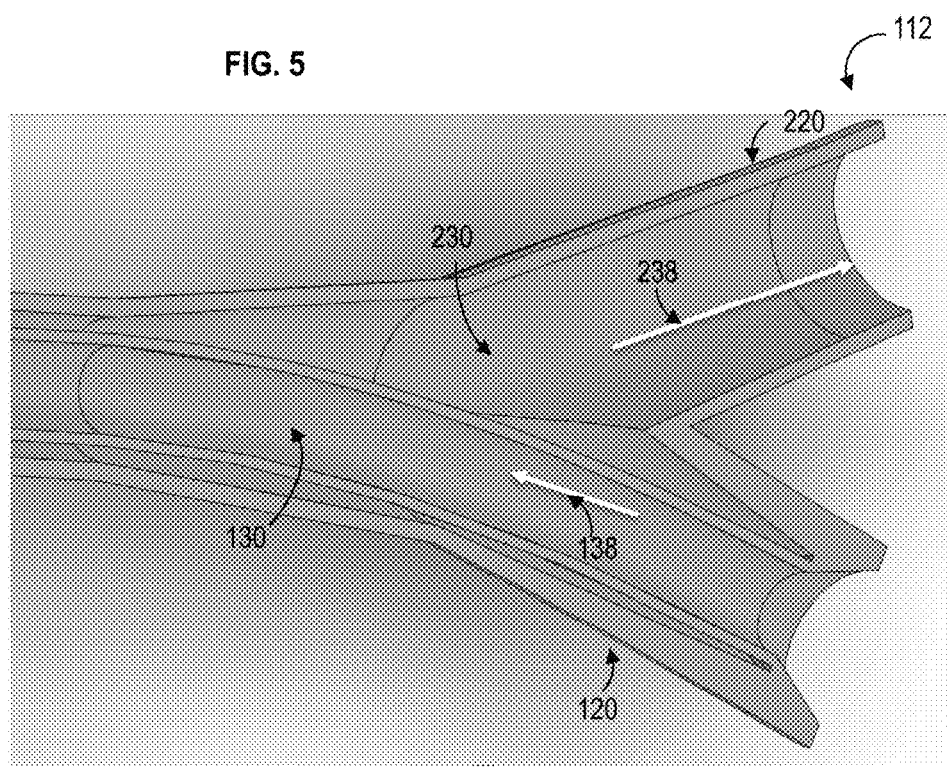
FIG. 5 shows a detailed view of the proximal end of the cannula.

As previously discussed, in some embodiments, the first lumen (130) is defined by the wall of the first tube (120). In some embodiments, the first lumen (130) is a separate channel from the first tube (120). In some embodiments, e.g., as shown in FIG. 5, the first lumen (130) is a separate channel from the first tube (120) and separate from the cannula (110). In some embodiments, the second lumen (230) is defined by the wall of the second tube (220). In some embodiments, the second lumen (230) is defined by the wall of the second tube (220) and at least a portion of the cannula (110), e.g., as shown in FIG. 5. In some embodiments, the second lumen (230) is a separate channel from the second tube (220) and/or cannula (110). In some embodiments, the second lumen (230) is the annular space between the first lumen (130) and the cannula (110) (and second tube (220).

As previously discussed, the first end (231) of the second lumen (230) is fluidly connected to the input of the cardiac assistance device (50), and the first end (131) of the first lumen (130) is fluidly connected to the output of the cardiac assistance device (50). A non-limiting example of the cardiac assistance device (50) includes an extracorporeal membrane pump (ECMO) device that is fluidly connected to the cannula (110) to remove deoxygenated blood (e.g., from the left ventricle) and return oxygenated blood (e.g., to the pulmonary artery). In some embodiments, the system (100) also comprises the cardiac assistance device (50) in addition to the cannula (110).

Figure 6:
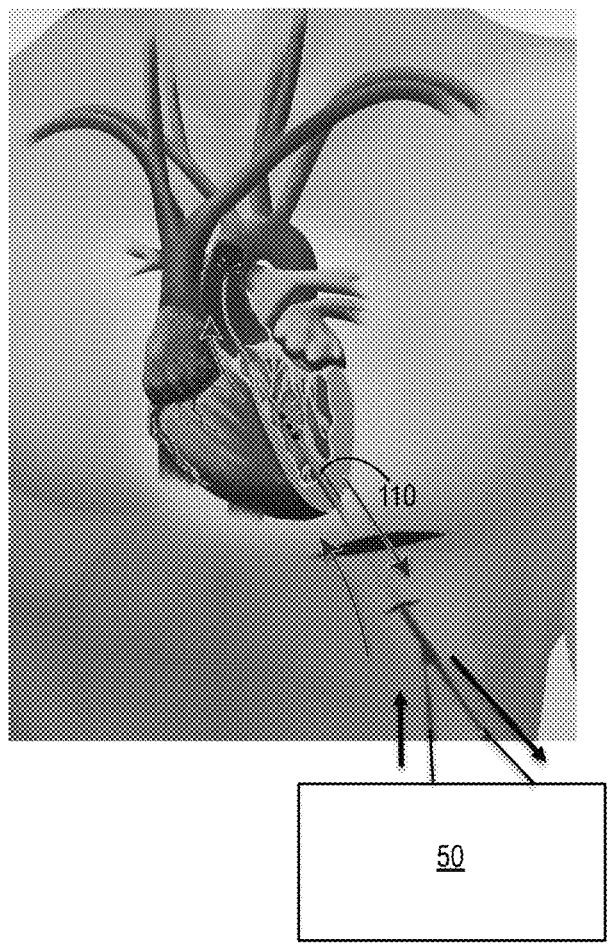
FIG. 6 shows a schematic view of the cannula coupled to an external cardiac assistance device.

As a non-limiting example, during a cardiac procedure, the cannula (110) may first be inserted into the left ventricle (60) and then further advanced such that the tip (118) of the cannula (110) is positioned in the aorta (70) and the intake apertures (114) are positioned in the left ventricle (60). More specifically, the tip (118) of the dual lumen cannula system (100) is inserted through the left ventricle (60), the aortic valve, and the left atrium of the heart such that the tip (118) is positioned in the aorta (70) without puncturing the aorta, and the intake apertures (114) are positioned entirely within the left ventricle (60). Herein, as shown in FIG. 6, the intake apertures (114) are within the walls of the left ventricle, not extending past the mitral valve into the left atrium, and also not extending past the aortic valve into the aorta. A length and configuration of the cannula (110) is selected such that the tip (118) and the intake apertures (114) are located in the aorta and left ventricle respectively. In addition, the proximal end (112) of the cannula (110) (e.g., the first end (131) of the first lumen (130) and first end (231) of the second lumen (230)) is located outside the patient, so as to allow the cardiac assistance device (50) to be fluidly connected to the cannula (110) (see FIG. 6).

When the system (100), e.g., the cannula (110), is inserted into the patient's heart and positioned and further coupled to the cardiac assistance device (50) as described above, the blood in the patient's heart begins circulating. More specifically, blood in the left ventricle (60) flows through the intake apertures (114), into the second lumen (230), and enters the cardiac assistance device (50) via the first end (231) of the second lumen (230). The blood that flows through the intake apertures (114) may be deoxygenated blood collected in the left ventricle. In this way, the intake apertures (114) positioned in the left ventricle (60) may drain the blood accumulated or collected in the left ventricle, thereby reducing left ventricular distention in the patient. The deoxygenated blood draining from the left ventricle (60) then flows to the cardiac assistance device (50) where the deoxygenated blood is oxygenated and returned, under pressure, back to the first lumen (130). As such, the blood returning from the device (50) into the first lumen (130) is oxygenated blood. The first arrow (138) shows the oxygenated blood flowing from the cardiac assistance device (50) into the first lumen (130), and the second arrow (238) shows the deoxygenated blood flowing from the second lumen (230) (e.g., the second tube (120)) to the cardiac assistance device (50).

The length of the first tube (120) may be longer than the length of the second tube (220). In some embodiments, the length of the first lumen (130) may be longer than the length of the second lumen (230). The length of the first lumen (130) may refer to the distance from the first end (131) to the second end (132), and the length of the second lumen (230) may refer to the distance from the first end (231) to the second end (232). Without wishing to limit the present invention to any theory or mechanism, when the length of the second lumen (230) is less than that of the first lumen (130), the intake apertures (114) may be entirely contained within the left ventricle (60). As a non-limiting example, the difference in lengths between the first lumen (130) and second lumen (230) may be about 80-100 mm. In some embodiments, the length of the first lumen (130) may be selected such that the first lumen (130) spans the entire length of the left ventricle and further extends into the aorta (but does not puncture the aorta) when the cannula (110) is inserted into the patient's heart.

In some embodiments, the inner diameter of the first tube (120) or first lumen (130) is 5 mm. In some embodiments, the outer diameter of the first tube (120) or first lumen (130) is 6.3 mm. In some embodiments, the inner diameter of the second tube is 8.2 mm. In some embodiments, the outer diameter of the second tube is 10.3 mm. The present invention is not limited to the dimensions disclosed herein. For example, in some embodiments, the inner diameter of the first tube (120) or first lumen (130) is from 4 to 6 mm, e.g., from 4.5 to 5.5 mm. In some embodiments, the inner diameter of the first tube (120) or first lumen (130) is from 3 to 8 mm. In some embodiments, the outer diameter of the first tube (120) or first lumen (130) is from 5 to 7 mm, e.g., from 5.9 to 6.4 mm. In some embodiments, the outer diameter of the first tube (120) or first lumen (130) is from 4 to 8 mm. In some embodiments, the inner diameter of the second tube is from 8 to 9 mm, e.g., from 8 to 8.5 mm. In some embodiments, the inner diameter of the second tube is from 7 to 10 mm. In some embodiments, the outer diameter of the second tube is from 10 to 11 mm, e.g., from 10 to 10.5 mm. In some embodiments, the outer diameter of the second tube is from 9 to 12 mm.

In some embodiments, the length of the first lumen (130) is 290 mm. In some embodiments, the length of the first lumen (130) is from 280 to 300 mm. In some embodiments, the length of the first lumen (130) is from 250 to 325 mm. In some embodiments, the length of the second lumen (230) is 90 mm. In some embodiments, the length of the second lumen (230) from 85 to 105 mm. In some embodiments, the length of the second lumen (230) from 60 to 120 mm. The values mentioned herein are examples only and are not meant to be limiting. Other values of the inner and outer diameters, and lengths of the first and the second tube may be used without deviating from the scope of the invention.

In some embodiments, the volume of the first lumen (130) may be equal to the volume of the second lumen (230). As such, the inner and outer diameters of the first tube (120), second tube (220), first lumen (130), and/or second lumen (230) may be designed such that a volumetric flow inside the second lumen (230) is equal to a volumetric flow inside the first lumen (130).

The intake apertures (114) function to drain the blood accumulated in the left ventricle. While flowing through the intake apertures (114), the blood may experience some shearing force. As such, the shearing forces may result in pushing some portions of the blood in one direction, and other portions of the blood in opposite direction. Such mechanical forces not only cause morphological changes of endothelium and blood vessel walls, but also trigger biochemical and biological events. For example, perturbation of the blood vessel walls may disturb biochemical homeostasis and lead to vascular remodeling and possible dysfunction (e.g. altered vasorelaxation, tone, stiffness, etc.). Herein, the intake apertures (114) may be oval in shape. Without wishing to limit the present invention to any theory or mechanism, the oval shape of the intake apertures (114) may be selected to reduce the shearing force on the blood vessel walls, and thus reduce platelet activation, for example.

Figure 7:
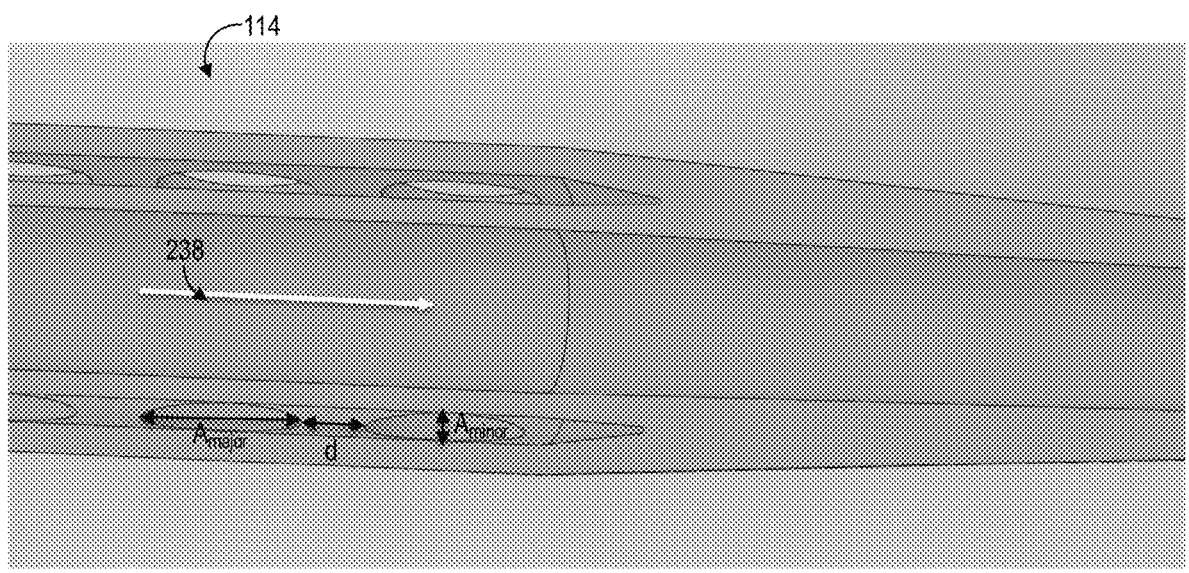
FIG. 7 shows a detailed view of intake apertures in the cannula of the dual lumen cannula system.

Each intake aperture (114) reduces the shear forces experienced by the blood flowing into the intake apertures (114). Referring to FIG. 7, each intake aperture (114) includes a major axis ($A_{major}$) aligned parallel to the direction of flow of blood in the second lumen (230) (indicated by arrow 238), and a minor axis ($A_{minor}$) which is orthogonal to the direction of blood flow in the second lumen (230). A ratio of the major axis ($A_{major}$) and the minor axis ($A_{minor}$) of each of the intake apertures (114) is configured to reduce a shear force on the blood sucked in from the left ventricle. As non-limiting examples, in some embodiments, the ratio is about 2.5 (e.g., the major axis may be about 5 mm and the minor axis may be about 2 mm). In some embodiments, the ratio is about 2. In some embodiments, the ratio is 3. In some embodiments, the ratio is from 2 to 3. In some embodiments, the ratio is from 3 to 4. In some embodiments, the ratio is from 4 to 5. In some embodiments, the ratio is from 1 to 10. In some embodiments, the ratio is from 5 to 10. In some embodiments, the ratio is from 1 to 25. In some embodiments, the ratio is from 10 to 25. In some embodiments, the ratio is from 1 to 50. In some embodiments, the ratio is from 10 to 50. In some embodiments, the ratio is from 1 to 100. In some embodiments, the ratio is from 50 to 100. In some embodiments, the ratio is from 1 to 500. In some embodiments, the ratio is from 100 to 500. In some embodiments, the ratio is from 500 to 1,000. In some embodiments, the ratio is from 1,000 to 5,000. In some embodiments, the ratio is from 5000 to 10,000. In some embodiments, the ratio is from 10,000 to 100,000. In some embodiments, the ratio is from 100,000 to 1,000,000. In some embodiments, the ratio greater than 100,000,000.

Comparison of shear rates and shear stress experienced by the blood flowing through circular or round holes versus oval holes is shown below in Table 1. Herein, the ratio of major axis and minor axis of the oval shaped hole is about 2.

TABLE 1

Shear Force and Velocity for Round and Oval Intake Apertures

|  | Round Intake Aperture | 2:1 ratio axes Oval Intake Aperture | Difference | Percent Change |
|---|---|---|---|---|
| Max Shear Rate [1/s] | 3245.5 | 3163.156 | −82.344 | −2.537174549 |
| Max Shear Stress [Pa] | 13.46 | 11.82 | −1.64 | −12.18424963 |
| Max Velocity [m/s] | 14.42 | 14.15 | −0.27 | −1.872399445 |
| Max Vorticity [1/s] | 799.28 | 822.5 | 23.22 | 2.905114603 |

As shown in Table 1, blood flowing through oval intake apertures experience lower shear rate and shear stress compared to blood flowing through round or circular intake apertures. For example, blood flowing through the oval intake apertures experiences about 2.5% lower shear rate and about 12.2% lower shear stress compared to blood flowing through the round hole. In addition, velocity of the blood flowing through the oval intake apertures is smaller than the velocity of blood flowing through the round intake apertures. Simulation of blood flowing across circular intake apertures and oval-shaped intake apertures is shown in FIG. 8A and FIG. 8B, respectively.

Referring to FIG. 8A, the path that the blood takes when it flows from a first region (1006) into a second region (1004) through a circular intake aperture (1008) is indicated as dots. When blood (1010) flows from the first region (1006) into the second region (1004) through the circular hole (1008), the blood experiences higher shearing force as seen by increased dots in the second region (1004). As described previously, the shearing forces may result in pushing some portions of the blood in one direction, and other portions of the blood in opposite direction. Such mechanical forces not only cause morphological changes of endothelium and blood vessel walls, but also trigger biochemical and biological events.

In contrast, when blood flows from the first region (1006) into the second region (1004) through an oval-shaped intake aperture (1016), the blood, as shown in FIG. 8B, experiences lower shearing force (as indicated by reduced number of dots in the second region (1004) of FIG. 8B). In addition, the flow of blood through the oval-shaped intake aperture is less turbulent, as indicated by the vectors in FIG. 8B. Thus, blood flowing through the oval-shaped intake apertures of the present invention experiences lower shear forces and therefore provides a hemodynamic way to reduce accumulation of blood in the left atrium and the left ventricle.

The intake apertures (114) may include a radially repeating pattern of a set of linear oval intake apertures (114). As non-limiting examples, the intake apertures (114) may be formed by having radially repeating pattern of a linear array of holes (114) extending for a threshold distance along the sidewall of the second lumen (230). As a non-limiting example, the intake apertures (114) may include 13 intake apertures spaced about 1 mm apart, and there may be 6 radial patterns of the intake apertures along the circumference of the second lumen (230). One or more of a linear spacing between individual intake apertures, a radial spacing between each linear array, and the ratio may be adjusted based on desired flow rate in the second lumen (230).

Blood flows into the system (100) though the intake apertures (114). By adjusting the parameters such as ratio, linear and radial spacing, shearing force experience by the blood as it enters the intake apertures is reduced. In addition, a shape and/or configuration of the tip (118) may be selected to reduce the shearing force experience as the blood exits the cannula, for example.

Figure 9:
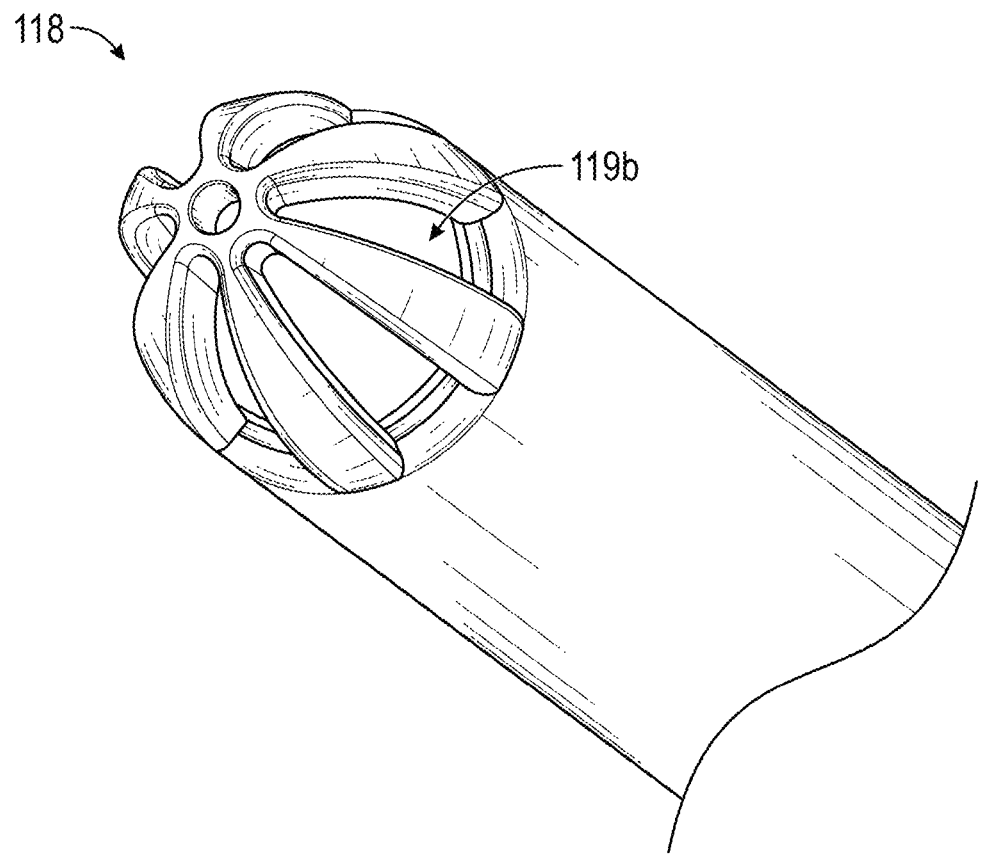
FIG. 9 shows a perspective view of the tip of the cannula.
Figure 10:
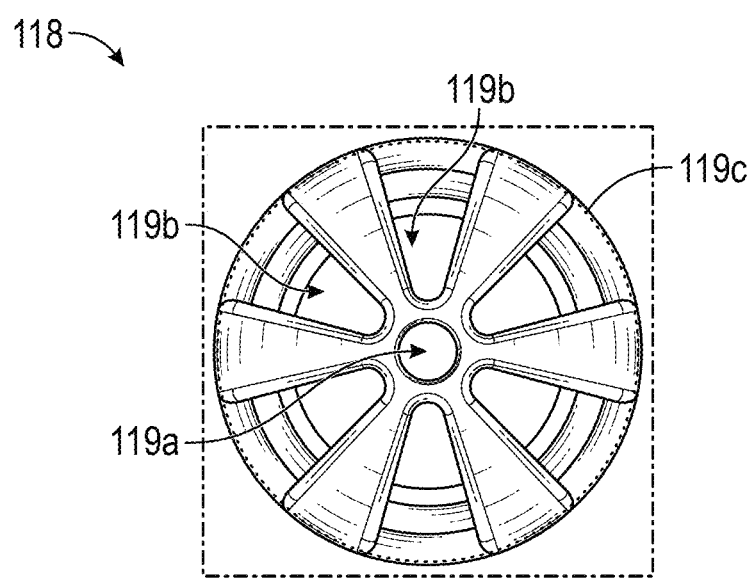
FIG. 10 shows the tip of FIG. 9 having a plurality of radially oriented slots.

Referring to FIG. 9 and FIG. 10, the tip (118) of the cannula (110) at the distal end (111) of the cannula (110) may be formed at the second end (132) of the first lumen (130). The tip (118) may feature a central hole (119a) for inserting a guide wire, and additionally include multiple radial slots (119b), through which blood exits the tip (118). As a non-limiting example, the slots (119b) may include a tapered shape to reduce the shearing force experience on the oxygenated blood delivered into the aorta. For example, the distal end of the slot (119b), e.g., the end closer to the central hole (119a), may be smaller in width than the width of the proximal end of the slot (119), e.g., the end of the slot closer to the outer edge (119c) of the tip (118). In some embodiments, the distal end of the slot (119b) may be curved or rounded. As a non-limiting example, in some embodiments, six slots (119b) are disposed in the tip (118). Other shapes and sizes of the slots (119b) configured to reduce the shearing force may be included without deviating from the scope of the invention.

Without wishing to limit the present invention to any theory or mechanism, it is believed that the radially oriented (and tapered) slots in the tip (118) and the oval-shaped intake apertures (114) help reduce shearing force on the blood exiting and entering the cannula (110).

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of oxygenating blood of a patient, said method comprising:
   a. using a dual lumen cannula system (100) for insertion in a heart of a patient, said system (100) comprising a cannula (110) with a distal end (111) and a proximal end (112), the cannula (110) comprises:
   a first tube (120) and a second tube (220) formed from bifurcation of the proximal end (112);
   a tip (118) disposed at the distal end (111), the tip (118) comprises at least one slot (119b); intake apertures (114) disposed in a side wall of the cannula (110) a distance from the tip (118), the intake apertures (114) are oval in shape;
   a first lumen (130) extending through the first tube (120) and the cannula (110), the first lumen (130) has a first end (131) for fluidly connecting to a cardiac assistance device (50) and a second end (132) fluidly connected to the at least one slot (119b) in the tip (118) of the cannula (110), wherein blood can pass from the first lumen (130) to outside the cannula (110) via the at least one slot (119) in the tip (118); and a second lumen (230) extending through the second tube (220) and at least a portion of the cannula (110), the second lumen (230) has a first end (231) for fluidly connecting to a cardiac assistance device (50) and a second end (232) fluidly connected to the intake apertures (114) in the side wall of the cannula (110), wherein blood can pass from outside the cannula (110) to the second lumen (230) via the intake apertures (114), the first lumen (130) is sealed from the second lumen (230); and a cardiac assistance device (50), wherein the first end (131) of the first lumen (130) is fluidly connected to an outlet port of the cardiac assistance device (50) and the first end (231) of the second lumen (230) is fluidly connected to an intake port of the cardiac assistance device (50);

b. inserting the tip (118) of the cannula (110) through a left ventricle, an aortic valve, and further through a left atrium of a heart of the patient such that the tip (118) of the cannula (110) is positioned in anaorta without puncturing the aorta, and the intake apertures are positioned within the left ventricle; and c. circulating blood through the cannula (110) and the cardiac assistance device (50), wherein deoxygenated blood from the left ventricle flows through the intake apertures (114) and into the second lumen (230), wherein the cardiac assistance device (50) intakes the deoxygenated blood from the second lumen (230), oxygenates said deoxygenated blood to form oxygenated blood, and pumps said oxygenated blood through the first lumen (130), and wherein oxygenated blood from the first lumen (130) exits the cannula (110) to the aorta via the tip (118), thereby providing oxygenated blood to the patient.

2. The method of claim 1, wherein the method reduces left ventricular distention in the patient.

3. The method of claim 1, wherein the method reduces shearing of the blood.

4. The method of claim 1, wherein the method reduces platelet activation.

5. The method of claim 1, wherein an inner wall of the second tube (220) defines the first end (231) of the second lumen (230).

6. The method of claim 1, wherein an inner wall of the cannula (110) and an outer wall of the first lumen (130) define the second lumen (230).

* * * * *